(12) United States Patent
Varga et al.

(10) Patent No.: US 12,246,134 B2
(45) Date of Patent: Mar. 11, 2025

(54) GAS VALVE FOR VENTILATION, A CIRCUIT FOR A VENTILATION SYSTEM AND A METHOD FOR DETERMINING A RELEASING GAS FLOW

(71) Applicants: IMTMEDICAL AG, Buchs (CH); Christopher M. Varga, Laguna Hills, CA (US)

(72) Inventors: Christopher M. Varga, Laguna Hills, CA (US); Martin Björn Hess, Malans (CH); Matthias Van Der Staay, Obstalden (CH)

(73) Assignee: IMTMEDICAL AG, Buchs (CH)

( * ) Notice: Subject to any disclaimer, the term of this patent is extended or adjusted under 35 U.S.C. 154(b) by 612 days.

(21) Appl. No.: 17/604,104

(22) PCT Filed: Apr. 10, 2020

(86) PCT No.: PCT/US2020/027570
§ 371 (c)(1),
(2) Date: Oct. 15, 2021

(87) PCT Pub. No.: WO2020/214490
PCT Pub. Date: Oct. 22, 2020

(65) Prior Publication Data
US 2022/0218939 A1    Jul. 14, 2022

(30) Foreign Application Priority Data
Apr. 15, 2019 (EP) ................................. 19169299

(51) Int. Cl.
*B01D 53/02*    (2006.01)
*A61M 16/00*    (2006.01)
(Continued)

(52) U.S. Cl.
CPC ...... *A61M 16/205* (2014.02); *A61M 16/0003* (2014.02); *A61M 16/085* (2014.02);
(Continued)

(58) Field of Classification Search
CPC ............ A61M 16/0003; A61M 16/085; A61M 16/0858; A61M 16/105; A61M 16/1055;
(Continued)

(56) References Cited

U.S. PATENT DOCUMENTS 4,239,038 A    12/1980 Holmes
4,403,514 A    9/1983 Osborn
(Continued)

FOREIGN PATENT DOCUMENTS

CN    103372256 A    10/2013
CN    203634619 U    6/2014
(Continued)

OTHER PUBLICATIONS

Intent to Grant Corresponding to EP 20722424.7 mailed Sep. 22, 2023.
(Continued)

*Primary Examiner* — Christopher P Jones
(74) *Attorney, Agent, or Firm* — Finch & Maloney PLLC

(57) ABSTRACT

A gas valve (11) for ventilation which comprises a main body (12) having a first gas chamber (13), a second gas chamber (15) and at least an inlet duct (14) for supplying a gas to the first gas chamber (13). The gas valve (11) further comprises a proportional valve (24) for temporally sealing the first gas chamber (13) from the second gas chamber (15). The second gas chamber (15) comprises at least a second passage opening (22) for releasing the gas from the second gas chamber (15) and the second gas chamber (15) comprises a port (30) for connecting a pressure measurement apparatus for measuring the gas pressure in the second gas (Continued)

Figure 1:
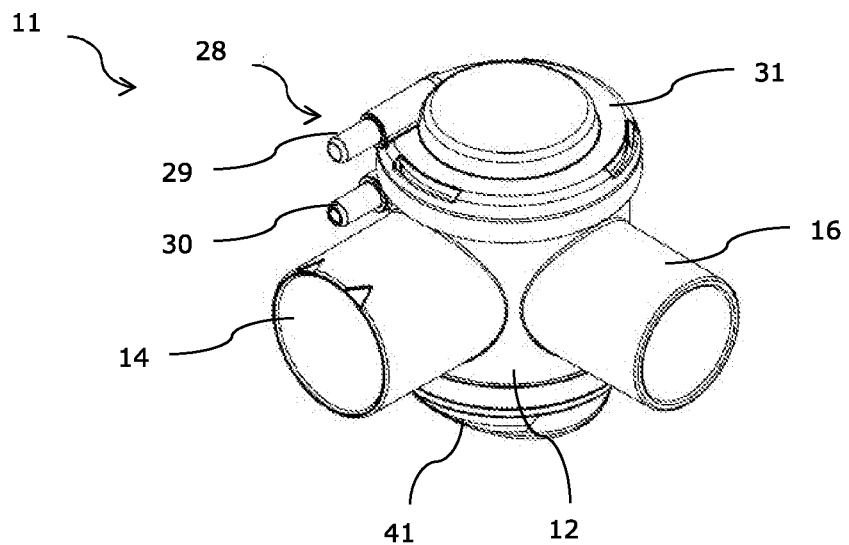

chamber (15). A circuit with a ventilation limb which comprises a gas valve (11) and a method for determining a releasing gas flow of a gas valve are also disclosed.

20 Claims, 4 Drawing Sheets

(51) Int. Cl.
*A61M 16/08* (2006.01)
*A61M 16/10* (2006.01)
*A61M 16/20* (2006.01)
*B01D 46/00* (2022.01)
*B01D 46/42* (2006.01)

(52) U.S. Cl.
CPC ...... *A61M 16/0858* (2014.02); *A61M 16/105* (2013.01); *A61M 16/206* (2014.02); *B01D 46/0087* (2013.01); *B01D 46/4236* (2013.01); *A61M 2016/0042* (2013.01); *A61M 2205/3313* (2013.01); *A61M 2205/3327* (2013.01); *A61M 2205/42* (2013.01)

(58) Field of Classification Search
CPC ............ A61M 16/1065; A61M 16/107; A61M 16/205; A61M 16/206; A61M 2016/0027; A61M 2016/0042; A61M 2202/0225; A61M 2205/3313; A61M 2205/3327; A61M 2205/3334; A61M 2205/42; A61M 2205/7509; A61M 2205/7518; B01D 46/0087; B01D 46/4236
See application file for complete search history.

(56) References Cited

U.S. PATENT DOCUMENTS

| | | | |
|---|---|---|---|
| 4,694,825 | A | 9/1987 | Slemmer et al. |
| 8,469,031 | B2 | 6/2013 | Winter et al. |
| 2011/0168181 | A1 | 7/2011 | Caspary |
| 2021/0001169 | A1* | 1/2021 | Roussel .............. A61M 16/201 |

FOREIGN PATENT DOCUMENTS

| | | |
|---|---|---|
| DE | 33 41 711 A1 | 5/1985 |
| EP | 1512426 A1 | 3/2005 |
| EP | 3 360 595 A1 | 8/2018 |
| FR | 2 535 612 A1 | 5/1984 |
| GB | 826 280 | 12/1959 |

OTHER PUBLICATIONS

International Search Report Corresponding to PCT/US2020/027570 mailed Aug. 5, 2020.
Written Opinion Corresponding to PCT/US2020/027570 mailed Aug. 5, 2020.

* cited by examiner

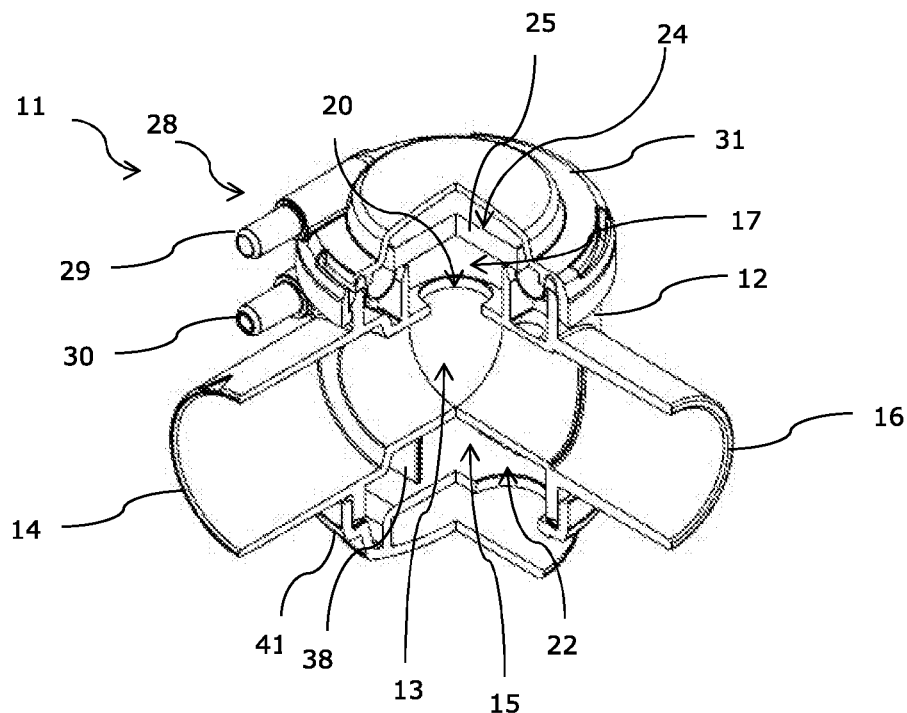
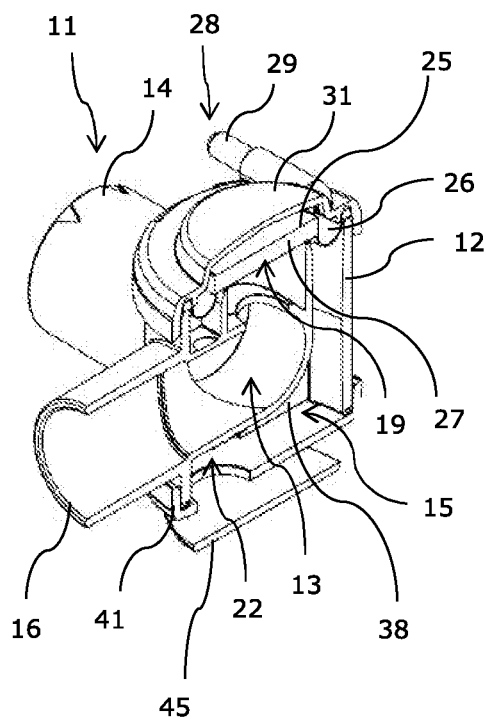
FIG 3
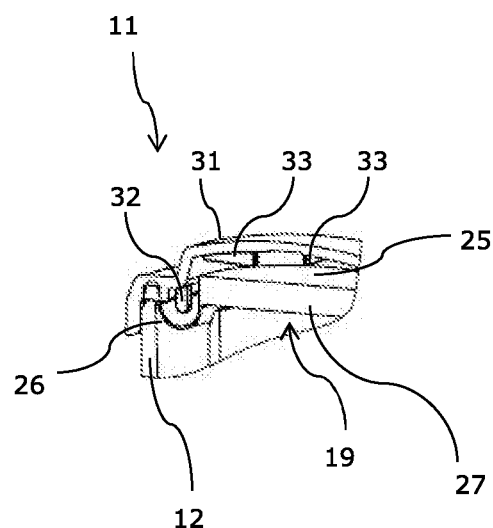
FIG 4
FIG 5

GAS VALVE FOR VENTILATION, A CIRCUIT FOR A VENTILATION SYSTEM AND A METHOD FOR DETERMINING A RELEASING GAS FLOW

The present invention relates to a gas valve for ventilation, a circuit for a ventilation system and a method for determining a releasing gas flow from a gas valve according to the independent claims.

During artificial respiration of a patient, it is desirable to prevent the patient from completely exhaling, and therefore the patient's lungs from fully deflating. This is because complete deflation, and subsequent reflation, of the patient's lungs requires a significant amount of the patient's energy. Prevention of total exhalation is generally achieved by including a mechanism in the respiratory circuit which only allows exhaled breath above an appropriate exhalation pressure to escape the respiratory circuit through a gas valve. Prevention of total exhalation in this way is known as applying "PEEP" to the respiratory circuit, where "PEEP" refers to "positive end-expiratory pressure".

Gas valves, like exhalation valves, concerning the state of the art can be used for breathing connections with two-way breathing to control the breathing gas. The exhalation air is directed to the ambient environment through the exhalation valve. The exhalation valve overpressure relief mechanism is typically made of an inflexible plastic disc, which is preloaded, e.g. via a spring. When exhaling, the exhalation valve only opens when the pressure of the exhaled gas (e.g. air) is greater than the preloaded pressure (e.g., >4.2 mbar) at the exhalation valve.

There are presently various forms of exhalation valves for respiratory breathing circuits.

EP 1 512 426 A1 comprises a gas valve for use with an exhalation port of a circuit. The valve comprising a sealed gas chamber, a gas inlet for supplying gas to the gas chamber, and a membrane defining at least part of a wall of the gas chamber. The membrane being situated, in use, adjacent to the exhalation port, and the membrane being deformable by a change in the pressure differential between the gas within the gas chamber and the gas within the exhalation port. Said gas valve is a simple exhalation valve for preventing a patient from total exhalation during artificial respiration.

CN 203634619 U discloses an exhalation gas control module comprising an exhalation valve with an exhalation chamber and a positive end-expiration chamber, a buffer throttle joint and a differential pressure sensor connected to a port of said exhalation valve. Said port comprises a check valve diaphragm to control the gas flow through said port to the differential pressure sensor. Said buffer throttle joint comprises a transition passage, which works as an additional buffer for the gas flow. When the pressure of said exhalation chamber is larger than the pressure in said positive end-expiration chamber, the gas may pass through said check valve diaphragm and leave said exhalation valve to said differential pressure sensor. Said differential pressure sensor is known as a gas flow sensor, which is described in the state of the art e.g. U.S. Pat. No. 4,403,514 A.

The aforementioned exhalation gas control module comprises many different components, which have to be produced individually and afterwards have to be arranged in a proper way to measure the exhalation gas flow of a patient during artificial respiration. Such an arrangement comprises many plug connectors and thus many possibilities for undesired leakage. Furthermore, said check valve diaphragm just seals the port of said exhalation valve to the environment or to said buffer throttle joint.

An aim of the invention is to avoid at least some of the drawbacks of the prior art, in particular, to provide a gas valve with a release gas flow measurement arrangement to increase the functionality of a gas valve. Furthermore, another aim of this invention is to provide a circuit comprising at least said gas valve for monitoring the release characteristics within the circuit. A further aim of this invention is a method to determine a releasing gas flow from said gas valve.

At least some of said aims are accomplished by a gas valve and a circuit for a ventilation system according as well as by a method to determine a releasing gas flow to the independent claims.

A gas valve for ventilation comprising a main body having a first gas chamber, a second gas chamber and at least an inlet duct for supplying a gas to the first gas chamber. The first gas chamber and the second gas chamber are connected at least by a first passage opening. Said gas valve comprises a proportional valve for temporarily sealing the first gas chamber from the second gas chamber, while the second gas chamber comprises at least a second passage opening for releasing the gas from the second gas chamber. The second gas chamber comprises a port for connecting a pressure measurement apparatus for measuring the gas pressure in the second gas chamber.

Such a gas valve can be used to determine a releasing gas flow by measuring the gas pressure in the second gas chamber and a subjacent calculation of said releasing gas flow through the second gas chamber. The releasing gas flow calculation can be determined by a differential gas pressure measurement, with at least a first gas pressure in said second gas chamber, measured via the port of said gas valve, and at least an ambient gas pressure as a second gas pressure. Therefore, said gas valve can be used to secure the ventilation process during artificial respiration and/or mechanical ventilation, while in addition said releasing gas flow in said second gas chamber is measured. This increases the functionality of said gas valve with a single port as connection to said pressure measurement apparatus and no additional gas flow sensor is necessary.

Complementary, said port can be used for electric measurements. These electric measurements can be used to determine said releasing gas flow in said second gas chamber by a gas flow measurement inside said second gas chamber and/or a subjacent calculation of said releasing gas flow in the second gas chamber.

Said gas valve can comprise an outlet duct for releasing the gas from the first gas chamber, while the proportional valve is closed (active operation). Said proportional valve omits a steady transition of the valve opening. Said outlet duct and said inlet duct advantageously form said first gas chamber. Therefore, a compact and simple gas valve can be provided, which is connectable directly to a pressure measurement apparatus via a pressure pipe. The said pressure pipe connects the port and said pressure measurement apparatus, which can be part of a ventilator apparatus.

The gas valve can be a pressure release valve. Said gas valve can be used to determine at least a part of the releasing gas flow by measuring the gas pressure in the second gas chamber and subjacent calculation of said releasing gas flow. Compared to an exhalation valve known in the state of the art, a pressure release valve is not contaminated by an exhalation gas from a patent during an artificial respiration. The gas entering and releasing said pressure release valve has not been in contact with a patient. In addition, said pressure release valve can be used as an exhalation valve. Therefore, said gas valve can be used to secure the exhalation process during artificial respiration, while in addition said releasing gas flow is measured. This increases the functionality of said gas valve.

Preferably said first gas chamber of said gas valve is at least partially surrounded by the second gas chamber. Therefore, a compact gas valve is provided, which is easy to produce. For example, an injection moulding method or additive manufacturing method, like rapid prototyping, can be used to produce said compact gas valve from a plastic material. The compact arrangement supports the pressure measurement in the said second gas chamber due to a short measurement path within said gas valve.

Further preferably the first passage opening comprises a smaller cross-section area compared to the cross-section area of the second passage opening. According to this embodiment, said proportional valve temporarily seals the first passage opening between the first gas chamber and the second gas chamber. Therefore, a stable valve characteristic can be achieved.

In particular the ratio of the cross-section area of the first passage opening and the cross-section area of the second passage opening is between 0.3 and 0.99, which leads to a stable valve characteristic and a sufficient measurement stability during said gas pressure measurement within the second gas chamber.

Furthermore, said ratio can be between 0.6 and 0.75, advantageously between 0.68 and 0.7. A gas pressure measurement with a stable characteristic can comprise e.g. a linear or a quadratic behaviour. In case of a linear behaviour, a characteristic pressure slope larger than 0 mbar/l/s is favourable. In case of a quadratic behaviour, a pressure drop larger than 0.1 cmH2O @a flow of 20 l/min can be achieved, which provides a reliable and reproducible gas valve performance. According to tests provided a preferred ratio is 0.69, which leads to an optimized characteristic slope of the gas pressure characteristic while the valve characteristic is stable.

Preferably an intermediate chamber is arranged between the first gas chamber and the second gas chamber, while the intermediate chamber comprises the first passage opening and a third passage opening. Said proportional valve can be assembled on said first passage opening to control the gas flow through said first passage opening during an exhalation process. Said intermediate gas chamber supports a repeatable control of the proportional valve even if the first passage opening is smaller than the second passage opening. A reliable and reproducible control of said proportional valve results in an enhanced gas pressure control in the first gas chamber.

Advantageously, the first passage opening comprises a larger cross-section area compared to the cross-section area of the third passage opening. Said proportional valve can be assembled to said first passage opening with large cross section. Therefore, a proportional valve with a common size can be used.

Furthermore, the third passage opening can comprise a smaller cross-section area compared to the cross-section area of the second passage opening, which leads to a stable valve characteristic.

In particular, the ratio of the cross-section area of the third passage opening and the cross-section area of the second cross-section area can be between 0.3 and 0.99, which leads to a stable valve characteristic and a sufficient measurement stability during said gas pressure measurement within the second gas chamber.

Furthermore, said ratio can be between 0.6 and 0.75, advantageously between 0.68 and 0.7. A gas pressure measurement with a stable characteristic can be achieved. In case of a linear behaviour, a characteristic pressure slope larger than 0 mbar/l/s is favourable. In case of a quadratic behaviour, a pressure drop larger than 0.1 cmH2O @a flow of 20 l/min can be achieved, which provides a reliable and reproducible gas valve performance.

According to tests provided a preferred ratio is 0.69, which leads to an optimized characteristic slope of the gas pressure characteristic while the valve characteristic is stable.

Further preferably, the cross-section area of at least one of the first passage opening, the second passage opening and/or third passage opening is controllable by an adjustment mechanism. Therefore, said ratio of at least one of said cross-sections is adjustable, which further increases the functionality of said gas valve. The releasing gas flow of an adult is different from the releasing gas flow of a baby. Therefore, gas valves with different dimensions have to be used for adults and for babies. Said gas valve can be used for adults as well as for babies. Said cross-section area can be adjusted manually before usage.

In particular, at least the first passage opening and the second passage opening are vertically separated within the gas valve. This arrangement leads to a compact gas valve and supports a repeatable gas flow measurement.

Preferably said second gas chamber comprises at least a dividing element for stabilizing the pressure measurement in the second gas chamber. Said dividing element suppresses undesirable gas flow behaviour within the second gas chamber and will support said gas pressure measurement. For an enhanced gas pressure measurement within said gas valve, a laminar gas flow within said second gas chamber is desirable to generate a predefined measurement path within the second gas chamber. Said dividing element can also be used as a guiding element for guiding the gas along the second gas chamber to the second passage opening.

Advantageously said dividing element comprises at least a rib. In particular a turbulent gas flow within the second gas chamber can be avoided by said rib. Therefore, said rib can provide a repeatable measurement of the gas pressure in the second gas chamber. Furthermore, an arrangement of more than one rib can be placed within the second gas chamber to enhance the formation of a laminar gas flow within said measurement path in said gas valve.

Alternative or complementary to said dividing element comprises at least a filter for protecting between the environment and the patient during artificial respiration.

Furthermore, said dividing element assembly can be exchangeable within said second gas chamber. Therefore, dividing elements with different dimensions can be assembled within said second gas chamber.

Advantageously, said port for connecting a pressure measurement apparatus for measuring the gas pressure in the second gas chamber is arranged at said second gas chamber, off the main gas flow through said second gas chamber. Said main gas flow centrally extends from the first passage opening, through the second gas chamber to the second passage opening. Due to the off-centre arrangement of said port, said pressure measurement occurs in said slipstream of the main gas flow in said second gas chamber.

Furthermore, said dividing element can be arranged adjacent to said main gas flow in said second gas chamber.

Therefore, said port for connecting a pressure measurement apparatus for measuring the gas pressure in the second gas chamber is divided from said main gas flow during an exhalation process, which enhances the reproducibility of said pressure measurements.

Further preferably said proportional valve is a membrane and can consist of a flexible material like a rubber material or a plastic material with flexible hinges. Such membranes are known in the state of the art.

Furthermore, said gas valve comprises advantageously a membrane control mechanism for controlling the membrane operation configuration between an inactive operation and an active operation. Said membrane control mechanism can be one of a pneumatic mechanism, an electric mechanism, a mechanical mechanism and/or a magnetic mechanism. In particular said control mechanism comprises a pressure control port. Said pressure control port can be connected to a control apparatus, like a ventilator apparatus, which controls the membrane operation configuration by applying a pressure to the membrane. Said pressure control port can be connected to said control apparatus by a pressure pipe. Said active operation of said membrane is defined by a pressurization of said membrane via said pressure control port, which leads to a temporary sealing of said first gas chamber from said second gas chamber. Said active operation of said membrane is provided during gas inhalation. Said inactive operation of said membrane is defined by a temporary unsealing of said first gas chamber from said second gas chamber, which leads to a gas flow through the second gas chamber during a gas exhalation process.

Preferably said membrane comprises an operation stabilizer for reducing an operation noise. Said stabilizer can comprise an additional mass element, embedded or connected to said membrane, which avoids a formation of a resonance frequency during operation and associated audible noise. Therefore, said gas valve enhances the working conditions during artificial respiration in hospitals as well as in private use. A difficulty with that flexible membrane type of valve is, however, that the flexibility of the diaphragm causes instability thereof, i.e. the membrane may not move uniformly from its seat but may flex only in a certain area thereof and thus release pressure in the patient circuit at a level unanticipated by the control pressure in the sealed chamber. If, on the other hand, the membrane is comprised of a rigid material to overcome the flexing problem, the rigid membrane does not allow good sealing against the valve opening and leakage is a further difficulty.

Further preferably the main body comprises a releasable lid for separating the proportional valve from the gas valve. Therefore, a proportional valve with different operational performance can be used within the same gas valve. Said releasable lid can be easily replaced from the main body. Said pressure control port of said membrane control mechanism can be arranged at said releasable lid.

In particular said lid comprises a membrane operation limitation and/or a membrane hinge stabilizer. Said operation limitation reduces the operation path of said membrane between said inactive operation and said active operation and leads to a higher switching speed during operation. Said operation limitation can be a bar or a pin, which is arranged at an inner side of said releasable lid. In addition, said membrane hinge stabilizer prevents a collapse of said membrane caused by an undesired pressure direction on the membrane. Said membrane hinge stabilizer can be at least a bar or at least a pin, which is arranged at said inner side of said lid and essentially at the edge of said lid. Said bar or pin essentially sticks into the direction of said membrane, when said lid is assembled on said main body. A combination of said membrane operation limitation and a membrane hinge stabilizer leads to an enhanced control of said membrane movement during operation.

Preferably said main body comprises a releasable cap for closing at least the second gas chamber. By releasing said cap from said main body, a direct access to said second gas chamber can be provided and said second gas chamber can be cleaned after usage of said gas valve. Furthermore, direct access to said dividing element is provided, which can be easily exchanged.

Advantageously said cap comprises at least the second passage opening. Therefore, caps with different second passage opening cross-sections can be placed at the gas valve, which leads to different ratios of the cross-section area of said second passage opening and the cross-section area of said third passage opening and therefore leads to different valve characteristics during said gas pressure measurements. Thus, a further increase of the flexibility and utility of said gas valve is provided.

Advantageously said second passage opening is arranged off the centre of said cap. Therefore, said second passage opening is arranged off said main gas flow through said second gas chamber, which leads to an enhanced pressure measurement.

Further preferably the releasable cap comprises at least a protection means for protecting the second passage opening at least partially from clogging. Thus, no limitation on the working position of said gas valve has to be considered, while a repeatable and stable gas pressure measurement is provided.

Advantageously the releasable cap comprises at least a cap opening. Said cap opening permits the release of said gas flow in the second gas chamber. Advantageously said cap comprises at least another cap opening, which prevents the second gas chamber from clogging.

Preferably the main body comprises a filter media for filtering the gas in the second gas chamber. Therefore, a contamination of the ventilator apparatus during the exhalation process can be avoided. In addition, said filter media is used to further reduce said operational noise during artificial respiration.

In particular the filter media is assembled in the releasable cap. Thus, said filter media can be exchanged from said gas valve. Furthermore, filter media with different properties can be used, e.g. different filter pore sizes and/or different filter materials.

In particular the filter media is assembled in the inlet duct of said main body. Thus, the filter media can easily be exchanged before said gas valve is connected to said ventilator apparatus.

Advantageously, the filter media is assembled in said second gas chamber. Therefore, the gas can be filtered before it can contaminate the ventilator apparatus and/or the environment. In particular said filter media is assembled in said second gas chamber as well as in said inlet duct and/or in said releasable cap. Said gas can be filtered in several parts of said gas valve, which leads to a sustainable filtration process.

According to a further embodiment of said invention, a circuit for a ventilation system comprises a ventilation limb and at least a gas valve according to any of the above-mentioned embodiments. Therefore, a circuit, which satisfies all standard safety requirements and with increased functionality can be disposed. In advantage, said gas valve enables the combination of an adjustable leakage and a release gas flow measurement within said circuit, while said gas valve can be used as an exhalation valve. Said circuit can be a single limb circuit or a dual limb circuit.

Preferably said gas valve is assembled at the distal end of the ventilation limb. Said distal end of said ventilation limb, generally, is connected directly to a ventilator apparatus. Said circuit comprises said gas valve, whereby said circuit is connected via said gas valve directly to said ventilator apparatus. Therefore, said port for connecting a pressure measurement apparatus for measuring the gas pressure and/or said membrane control port of said gas valve can be easily connected to the ventilator apparatus via said pressure pipes/tubes. Thus, short pressure pipes/tubes can be used during operation. Furthermore, the work of breathing of the patient during artificial respiration is reduced. In addition, said gas valve can be uses as a pressure release valve and will be not contaminated by an exhalation gas during artificial respiration.

Alternative or complementary, a carbon dioxide measurement is connected to the circuit. Therefore, a carbon dioxide concentration or carbon dioxide clearance can be determined at said circuit.

Advantageously said carbon dioxide measurement is assembled in the gas valve, which further increases the functionality of said gas valve.

In particular said carbon dioxide measurement is a colorimetric carbon dioxide indicator. Therefore, said carbon dioxide concentration or carbon dioxide clearance performance can be visualized. Said colorimetric carbon dioxide indicator can be a strip, a grid and/or a graduated scale for easy visualization of said carbon dioxide concentration or carbon dioxide clearance performance with said gas valve.

Further preferably, a further leakage is placed at the proximal end of the ventilation limb, while the further leakage can either be a fixed leakage or an adjustable leakage. Said proximal end of the ventilation limb is connected to a respiration mask or a respiration cannula for a patient for artificial respiration. A simple fixed leakage consists of a hole in said ventilation limb. An adjustable leakage comprises e.g. another gas valve, like an above-mentioned gas valve. Therefore, a standardized carbon dioxide concentration or carbon dioxide clearance can be enabled.

According to a further aspect of the invention a method for determining a releasing gas flow of a gas valve with a main body having a first gas chamber, a second gas chamber and at least an inlet duct, while the first gas chamber and the second gas chamber are connected at least by a first passage opening and a proportional valve for temporally sealing the first gas chamber from the second gas chamber, while said method comprises the at least the following steps:

supplying a gas to the first gas chamber through said inlet duct in a first direction, while said proportional valve is in an active operation configuration;

supplying a gas to the first gas chamber in a second direction, while said proportional valve is in an inactive operation configuration;

measuring the gas pressure in the second gas chamber with a pressure measurement apparatus;

determining a releasing gas flow based on said measured gas pressure in said second gas chamber.

Said method can be used to secure the ventilation process during artificial respiration and/or mechanical ventilation, while in addition said releasing gas flow in said second gas chamber is determined. This increases the functionality of said gas valve and no additional gas flow sensor is necessary.

In particular said gas valve is the above described gas valve. Therefore, said a compact gas valve can be used to reliably determine said releasing gas flow in said second gas chamber.

Preferably, the proportional valve is a membrane and furthermore is pressurized by a positive pressure to stay in said active operation configuration. Therefore, said membrane can be easily controlled by a membrane control mechanism.

In particular, during said change of the operation configuration of said proportional valve from active operation to inactive operation at least said first passage opening between said first gas chamber and said second gas chamber will be opened, while in in the contrary case said at least said first passage opening will be sealed.

Further preferably, said opening of at least the first passage is performed by lifting said membrane from the active operation configuration to the inactive operation configuration by either said gas supplied in the second direction or by said membrane control mechanism.

Preferably, said releasing gas flow can be determined by a differential gas pressure measurement, with at least a first gas pressure in said second gas chamber, measured via a port of said gas valve, and at least an ambient gas pressure as a second gas pressure. This further increases the functionality of said gas valve with a single port as connection to said pressure measurement apparatus and no additional gas flow sensor is necessary.

Further preferably, carbon dioxide is measured in the second gas chamber of said gas valve. Therefore, a carbon dioxide concentration or carbon dioxide clearance can be determined with said gas valve.

In particular, a colorimetric carbon dioxide indicator is used to determine said carbon dioxide concentration. Therefore, said carbon dioxide concentration or carbon dioxide clearance performance can be visualized.

Further advantageous aspects of the invention are explained in the following by means of exemplary embodiments and the figures. In the drawings, it is shown in a schematic manner. Furthermore, a numeric counting within this application is just used to differ between said parts of said gas valve.

Figure 2:
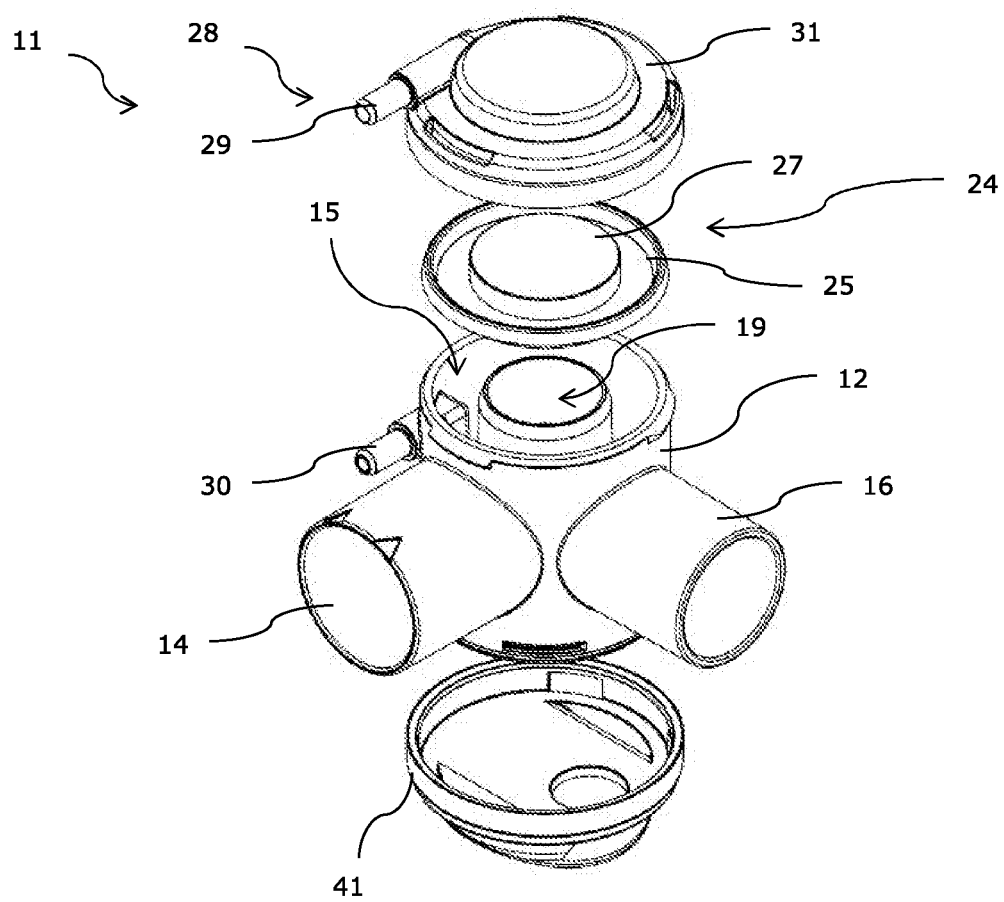
Figure 6:
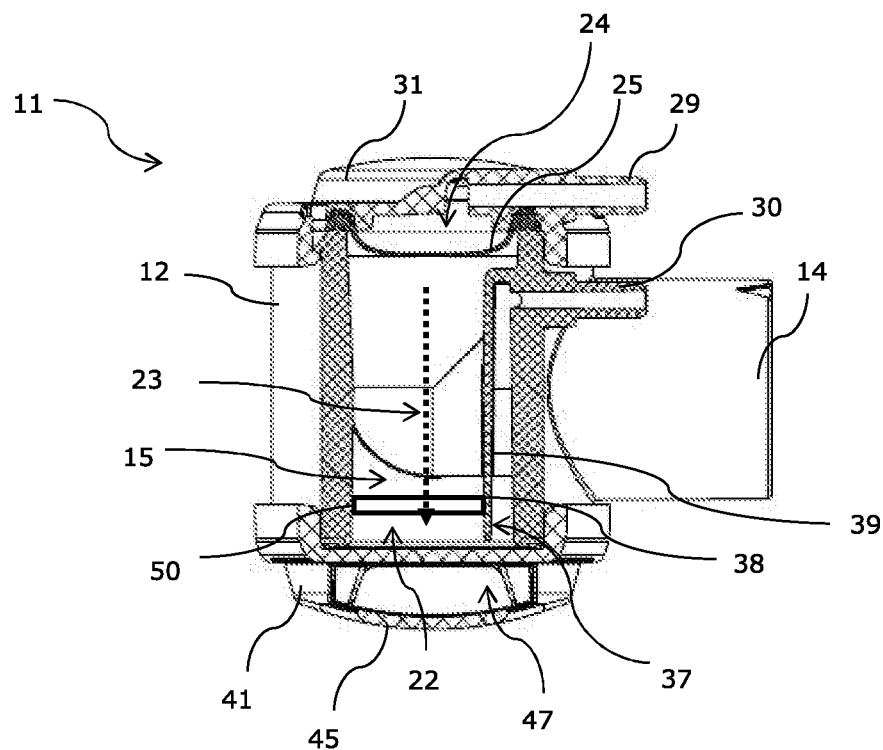
Figure 7:
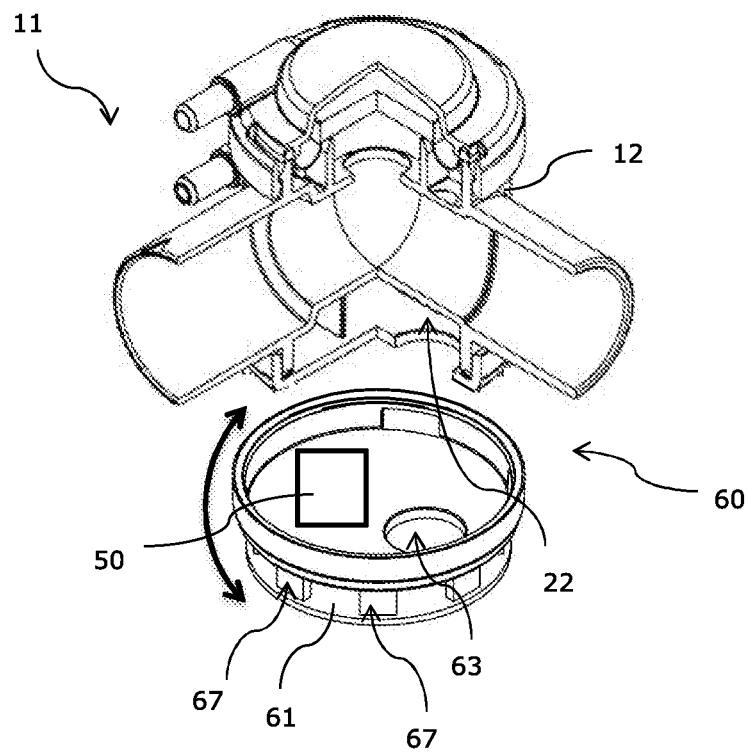

FIG. 1: A first embodiment of a gas valve in a perspective view,

FIG. 2: individual part of said gas valve of FIG. 1 in an exploded-view,

FIG. 3: said gas valve of FIG. 1 in a first cutaway view,

FIG. 4: said gas valve of FIG. 1 in a second cutaway view,

FIG. 5: parts of said gas valve of FIG. 1 in a third cutaway view,

FIG. 6: said gas valve of FIG. 1 in a cross-section view,

FIG. 7: a further embodiment of said gas valve of FIG. 1 an exploded-view

Figure 8:
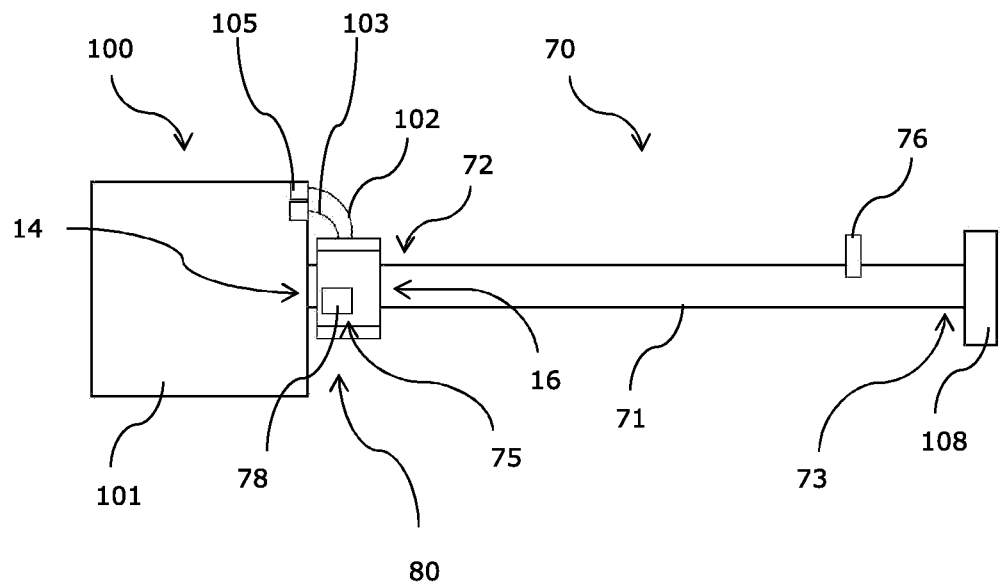
Figure 9:
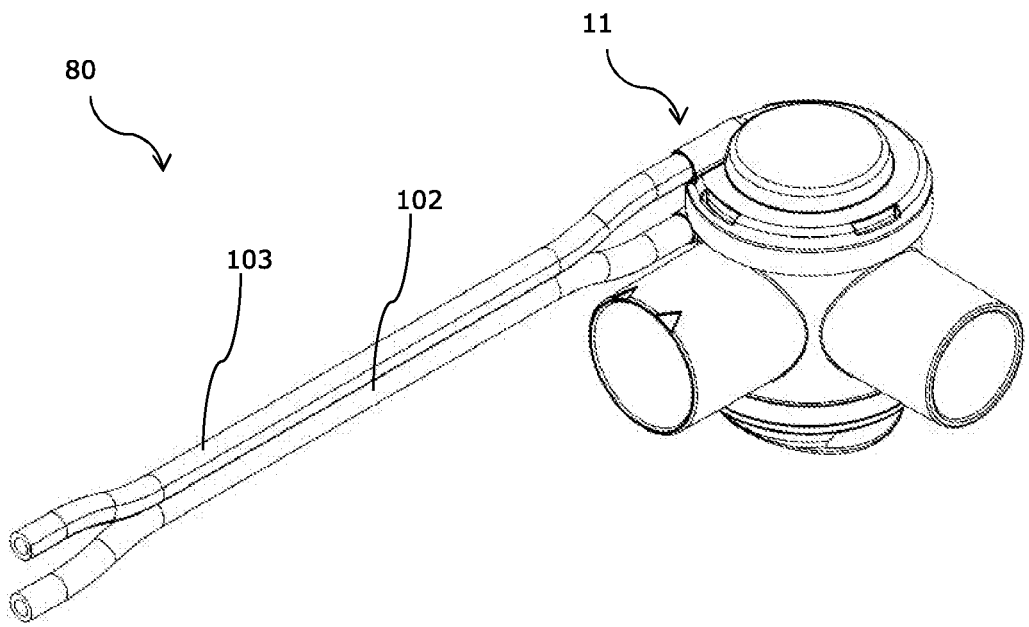

FIG. 8: a circuit comprising at least a gas valve of the previous mentioned Figures in a schematic view, and FIG. 9: an assembly with said gas valve of FIG. 1 in a perspective view.

FIG. 1 to FIG. 3 shows a first embodiment of a gas valve 11 comprising a main body 12 having a first gas chamber 13, a second gas chamber 15, an inlet duct 14 for supplying a gas to the first gas chamber 13 and an outlet duct 16 for releasing the gas from the first gas chamber 13. Said inlet duct 14 and said outlet duct 16 form said first gas chamber 13 within the main body 12. The first gas chamber 13 and the second gas chamber 15 are connected by an intermediate gas chamber 17 and a first passage opening 19. Said second gas chamber 15, which is placed within said main body 12, comprises a port 30 for connecting a pressure measurement apparatus for measuring the gas pressure in the second gas chamber 15. Furthermore, said second gas chamber 15 comprises a second passage opening 22 for releasing the gas from the second gas chamber 15 to the ambient environment.

Said first gas chamber 13 and said second gas chamber 15 are arranged in said main body 12, while said first gas chamber 13 is at least partially surrounded by the second gas chamber 15. The compact arrangement supports the pressure measurement in the said second gas chamber 15 due to a short measurement path within said gas valve 11. This preferred embodiment of said gas valve 11 comprises said intermediate gas chamber 17, which is arranged between the first gas chamber 13 and the second gas chamber 15. Said intermediate gas chamber 17 comprises said first passage opening 19 and a third passage opening 20. The first passage opening 19 and the second passage opening 22 as well as the third passage opening 20 are vertically separated within the assembled gas valve 11.

The first passage opening 19 comprises a larger cross-section area compared to the cross-section area of the third passage opening 20. Said third passage opening 20 comprises a smaller cross-section area compared to the cross-section area of the second passage opening 22. The ratio of the cross-section area of the third passage opening 20 and the cross-section area of the second passage opening 22 is about 0.69, which leads to a stable valve characteristic and an optimized characteristic slope of the gas pressure characteristic during the gas pressure measurement.

In addition, said gas valve 11 comprises a releasable lid 31 and releasable cap 41 and therefore comprises three main parts (main body 12, lid 31 and cap 41), which can be separated from each other (see FIG. 2). Said three main parts are made of plastic most properly produced by an injection moulding method. FIG. 1 shows said gas valve 11 in an assembled condition, while FIG. 2 shows the individual parts of said gas valve 11.

In an alternative embodiment of said gas valve 11, said intermediate gas chamber can be omitted (not shown). The remaining parts of the above-mentioned gas valve 11 are unchanged. Such an embodiment of said gas valve comprises just one passage opening (as a first passage opening) for above-mentioned first passage opening and said third passage opening, which is arranged between a first gas chamber and a second gas chamber. The ratio of the cross-section area of first passage opening and the cross-section area of the second passage opening can be also 0.69.

FIGS. 4 and 5 show the above-mentioned gas valve 11 comprising a membrane 25 as a proportional valve 24 for temporarily sealing the first gas chamber 13 from the second gas chamber 15. Said membrane 25 is made of a flexible material like a rubber material or a plastic material with flexible hinges 26. Said membrane 25 is assembled on said first passage opening 19 to control the gas flow through said first passage opening 19 during an exhalation process. Said membrane 25 comprises an operation stabilizer 27 for reducing an operational noise. Said stabilizer 27 comprises an additional mass element, embedded or connected to said membrane 25, which avoids a formation of a resonance frequency during operation. Said membrane 25 is replaceable in the assembly of said gas valve 11. Therefore, membrane 25 with different operation stabilizers 27 can be used within said gas valve 11.

The gas valve 11 comprises a membrane control mechanism 28 for controlling the membrane operation configuration between an inactive operation and an active operation. Said membrane control mechanism 28 is a pneumatic mechanism comprising a pressure control port 29. Said pressure control port 29 can be connected to a control apparatus, like a ventilator apparatus, which controls the membrane operation configuration by pressurizing said membrane 25 from one side. Said pressure control port 29 can be connected to said control apparatus by a pressure pipe/tube (see FIG. 8 and FIG. 9). Said membrane 25 seals said first passage opening 19 by pressurizing the membrane 25 with a positive pressure threshold via said pressure control port 29. While pressurizing, said membrane 25 is activated (active operation). Otherwise said membrane 25 is inactive and can be lifted by a positive pressure in said first gas chamber 13 during an exhalation process (inactive operation).

FIG. 5 shows said releasable lid 31, which comprises membrane operation limitations 33 and a membrane hinge stabilizer 32. Said operation limitations 33 reduces the operation path of said membrane 25 between said inactive operation and said active operation configuration. Said operation limitations 33 are bars, which are placed at an inner side of said releasable lid 31. In addition, said membrane hinge stabilizer 32 prevents a collapse of said membrane 25 caused by an undesired pressure direction on the membrane 25. Said membrane hinge stabilizer 32 comprises a bar, which is arranged at said inner side of said lid 31 and essentially at the edge of said lid 31. Said bar essentially sticks into the direction of said operation stabilizers 27 of said membrane 25, if said lid 31 is assembled on said main body 12.

FIG. 6 shows a cross-section view of the above-mentioned assembled gas valve 11 for ventilation to further disclose said second gas chamber 15. Said port 30 for connecting a pressure measurement apparatus for measuring the gas pressure in the second gas chamber 15 is arranged at said second gas chamber 15, off the main gas flow 23 through said second gas chamber 15. Said main gas flow 23 centrally extends from the first passage opening 19, through the second gas chamber 15 to the second passage opening 22. Said second gas chamber 15 comprises a dividing element 37 for stabilizing the pressure measurement in the second gas chamber 15. Said dividing element 37 is arranged adjacent to said main gas flow 23 in said second gas chamber 15. Said dividing element 37 can also be used as a guiding element for guiding the gas along the second gas chamber 15 to the second passage opening 22. Said dividing element 37 comprises at least a rib 38. Said rib 38 can be exchangeable within the assembly of said second gas chamber 15. Said dividing element 37 can at least partially consist of a filter 39. The gas valve 11 comprises a releasable cap 41 for closing at least the second gas chamber 15. By releasing said cap 41 from said main body 12, a direct access to said second gas chamber 15 is provided. Said cap 41 comprises the second passage opening 22 and a protection means 45 for protecting the second passage opening 22 at least partially from clogging. In addition, said releasable cap 41 comprises cap openings 47 for releasing said gas flow from the second gas chamber 15. Said second passage opening 22 is arranged off said centre of said cap 41. Therefore, said second passage opening 22 is arranged asymmetric to said main gas flow 23 through said second gas chamber 15.

The gas valve 11 furthermore can comprise a filter media 50 for filtering the gas in the second gas chamber 15 within the main body 12. Said filter media 50 can be assembled in the releasable cap 41 (not shown). Alternatively, said filter media 50 is assembled in the inlet duct 14 of said main body 12.

FIG. 1 to FIG. 6 are in addition used to disclose a method for determining a releasing gas flow from said gas valve 11. During inhalation, an inhalation gas is supplied to the first gas chamber 13 through said inlet duct 14 and said outlet duct 15 in a first direction. Said membrane 25, as a proportional valve, is in an active operation configuration due to said pressurization of said membrane 25 by a threshold pressure from one side via said pressure control port 29. Afterwards, during exhalation, an exhalation gas is supplied to the first gas chamber 13 through said outlet duct 16 in a second direction. Said first direction is essentially inverse to said second direction. In addition, said membrane 25 is in an inactive operation configuration, while no threshold pressure via said pressure control port 29 is applied to said membrane 25. Said exhalation gas opens at least the first passage opening 19 between said first gas chamber 13 and said second gas chamber 15 by lifting said membrane 25 with the positive exhalation pressure. Said exhalation gas flows, as main gas flow 23, through said second chamber 15 to said second passage opening 22 comprising a certain gas pressure. Said gas pressure is measured in the second gas chamber 15 with a pressure measurement apparatus, which is connected via said port 30 and a pressure pipe/tube 102 to said second gas chamber 15 (see FIG. 8 or FIG. 9). Said pressure measurement apparatus comprises a control unit, e.g. a processor (not shown) to determine said releasing gas flow based on said measured gas pressure in said second gas chamber 15. For example, said releasing gas flow is determined by a differential gas pressure measurement, with at least a first gas pressure in said second gas chamber 15, measured via said port 30 of said gas valve 11, and at least an ambient gas pressure as a second gas pressure.

FIG. 7 shows a further embodiment of the above-mentioned gas valve 11, additionally comprising an adjustment mechanism 60 for adjusting the effective cross-section of said second passage opening 22. Said adjustment mechanism 60 comprises a cap 61 with cap openings 67, which can be assembled to the main body 12 of said gas valve 11. Said cap 61 is twistable around the central longitudinal axes of said main body 12 of said gas valve 11 and comprises a control opening 63 for adjusting the effective cross-section area of said second passage opening 22. Therefore, said abovementioned ratio of said cross-section areas are adjustable. Said cap 61 may additionally comprise said filter media 50 for filtering the gas and for damping the noise during operation. Said filter media 50 may consist of a foam material. The above-mentioned parts of said gas valve 11 remain unchanged (see FIG. 1 to FIG. 6).

FIG. 8 shows a circuit 70 for a ventilation system 100 comprising a ventilation limb 71 and at least a gas valve 11 to any of the above-mentioned embodiments. Said gas valve 11 is assembled at the distal end 72 of the ventilation limb 71 with said outlet duct 16 and is used as a pressure release valve. Said circuit 70 is connected via said inlet duct 14 of said gas valve 11 to said ventilator apparatus 101. Said inlet duct 14 can comprise an above-mentioned filter media. Therefore, the above-mentioned port for connecting a pressure measurement apparatus 105 for measuring the gas pressure and/or said pressure control port 29 of said gas valve 11 are connected to the ventilator apparatus 101 via said pressure pipes/tubes 102 and 103. A carbon dioxide measurement 75 is assembled to said circuit 70, which is a colorimetric carbon dioxide indicator 78, assembled at said gas valve 11. Said colorimetric carbon dioxide indicator 78 is a strip and consists of a paper or thin chemical substrate which changes colour depending upon the carbon dioxide threshold within the breathing gas in said gas valve 11.

Alternatively, said indicator may consist of a grid and/or comprises a carbon dioxide scale. In addition to the above-mentioned method for determining said releasing gas flow from said second gas chamber 15, the carbon dioxide is measured in the second gas chamber 15 of said gas valve 11 during exhalation.

In addition, a further leakage 76 is placed at the proximal end 73 of the ventilation limb 71. Said proximal end 73 of the ventilation limb 71 is connected to a respiration mask 108.

During an inhalation process, an inhalation gas will pass the pressure release valve through said inlet duct 14 and outlet duct 16 and afterwards will reach via said ventilation limb 71 a patient. During an exhalation process, an exhalation gas will leave said ventilation limb 71 through said further leakage 76 and will not contaminate said pressure release valve. Nevertheless, part of said exhalation gas will pressurize the remaining gas in the ventilation limb 71 during said exhalation process, which is measured in the gas valve 11 for measuring said gas pressure and calculating said release gas flow in said second gas chamber 15.

FIG. 9 shows an assembly 80 with said gas valve 11, according to one of the above-mentioned embodiments (FIG. 1 to FIG. 6 or FIG. 7). The assembly 80 comprises the above-mentioned pressure pipes/tubes 102 and 103, which are connected to the above-mentioned pressure control port 29 and port 30.

LIST OF REFERENCES 11 gas valve
12 main body of 13
13 first gas chamber
14 inlet duct
15 second gas chamber
16 outlet duct
17 intermediate gas chamber
19 first passage opening
20 third passage opening
22 second passage opening
23 main gas flow through 15
24 proportional valve
25 membrane
26 flexible hinges of 25
27 operation stabilizer
28 membrane control mechanism
29 pressure control port
30 port
31 lid
32 membrane hinge stabilizer
33 membrane operation limitations
37 dividing element
38 rib
39 filter
41 cap
45 protection means
47 cap opening of 41
50 filter media
60 adjustment mechanism
61 cap
63 control opening
67 cap openings of 61
70 circuit
71 ventilation limb
72 distal end of 71
73 proximal end 71
75 carbon dioxide measurement 76 leakage
78 colorimetric carbon dioxide indicator
80 assembly
100 ventilation system
101 ventilator apparatus
102 pressure pipe/tubes
103 pressure pipe/tubes
105 pressure measurement apparatus
108 respiration mask

The invention claimed is:

1. A pressure release valve for ventilation comprising:
a main body having a first gas chamber, a second gas chamber, at least an inlet duct for supplying a gas to the first gas chamber and an outlet duct for releasing the gas from the first gas chamber, whereby said outlet duct and said inlet duct form said first gas chamber,
wherein the first gas chamber and the second gas chamber are connected at least by a first passage opening,
a proportional valve for temporally sealing the first gas chamber from the second gas chamber, while the second gas chamber comprises at least a second passage opening for releasing the gas from the second gas chamber, and
the second gas chamber comprises a port for connecting a pressure measurement apparatus for measuring the gas pressure in the second gas chamber.

2. The pressure release valve according to claim 1, wherein the first gas chamber is at least partially surrounded by the second gas chamber.

3. The pressure release valve according to claim 1, wherein the first passage opening comprises a smaller cross-sectional area, compared to a cross-sectional area of the second passage opening, while a ratio of the cross-sectional area of the first passage opening and the cross-sectional area of the second passage opening is between 0.3 and 0.99.

4. The pressure release valve according to claim 1, wherein an intermediate chamber is arranged between the first gas chamber and the second gas chamber, while the intermediate chamber comprises the first passage opening and a third passage opening.

5. The pressure release valve according to claim 4, wherein the first passage opening comprises a larger cross sectional area compared to the third passage opening, while a ratio of a cross-sectional area of the third passage opening and the cross-sectional area of the second passage opening is between 0.3 and 0.99.

6. The pressure release valve according to claim 1, wherein the cross-sectional area of at least one of the first passage opening, the second passage opening and/or the third passage opening is controllable by an adjustment mechanism.

7. The pressure release valve according to claim 1, wherein at least the first passage opening and the second passage opening are vertically separated within the pressure release valve.

8. The pressure release valve according to claim 1, wherein the second gas chamber comprises at least a dividing element for stabilizing the pressure measurement in the second gas chamber.

9. The pressure release valve according to claim 8, wherein the dividing element comprises at least one of at least a rib and/or a filter.

10. The pressure release valve according to claim 1, wherein the proportional valve is a membrane and the pressure release valve comprises a membrane control mechanism for controlling a membrane operation configuration at least between an inactive operation and an active operation.

11. The pressure release valve according to claim 10, wherein the membrane comprises an operation stabilizer for reducing operation noise.

12. The pressure release valve according to claim 1, wherein the main body comprises a releasable lid for separating the proportional valve from the pressure release valve, while the lid comprises at least one of a membrane operation limitation and/or a membrane hinge stabilizer.

13. The pressure release valve according to claim 1, wherein the main body comprises a releasable cap for closing at least the second gas chamber.

14. The pressure release valve according to claim 13, wherein the releasable cap comprises at least the second passage opening.

15. The pressure release valve according to claim 13, wherein the releasable cap comprises at least a protection means for at least partially protecting the second passage opening from clogging, and the releasable cap comprises at least a cap opening.

16. The pressure release valve according to claim 1, wherein the main body comprises a filter media for filtering the gas in the second gas chamber, while the filter media is assembled in one of a releasable cap, the inlet duct, or the second gas chamber.

17. A circuit for a ventilation system comprising a ventilation limb and at least a pressure release valve according to claim 1.

18. The circuit according to claim 17, wherein the pressure release valve is assembled at the distal end of the ventilation limb and/or a carbon dioxide measurement is connected to the circuit, while the carbon dioxide measurement is assembled in the pressure release valve, and is a colorimetric carbon dioxide indicator.

19. The circuit according to claim 17, wherein a leakage is assembled at a proximal end of the ventilation limb, while the leakage can either be a fixed leakage or an adjustable leakage.

20. A method for determining a releasing gas flow of the pressure release valve according to claim 1, said method comprises the at least the following steps:
supplying the gas to the first gas chamber through said inlet duct in a first direction, while said proportional valve is in an active operation configuration;
supplying the gas to the first gas chamber in a second direction through said outlet duct, while said proportional valve is in an inactive operation configuration;
measuring the gas pressure in the second gas chamber with a pressure measurement apparatus; and
determining a releasing gas flow based on said measured gas pressure in said second gas chamber.

* * * * *